United States Patent [19]

Karube et al.

[11] Patent Number: 4,789,804
[45] Date of Patent: Dec. 6, 1988

[54] ANALYTICAL DEVICE AND METHOD UTILIZING A PIEZOELECTRIC CRYSTAL BIOSENSOR

[75] Inventors: Isao Karube, Tachikawa; Hiroshi Muramatsu, Tokyo, both of Japan

[73] Assignee: Seiko Instruments & Electronics Ltd., Tokyo, Japan

[21] Appl. No.: 908,371

[22] Filed: Sep. 17, 1986

[30] Foreign Application Priority Data

| Sep. 17, 1985 | [JP] | Japan | 60-204949 |
| Mar. 10, 1986 | [JP] | Japan | 61-51657 |
| Mar. 10, 1986 | [JP] | Japan | 61-51658 |
| May 21, 1986 | [JP] | Japan | 61-116626 |
| Jun. 6, 1986 | [JP] | Japan | 61-131481 |
| Jun. 6, 1986 | [JP] | Japan | 61-131482 |

[51] Int. Cl.$^4$ .................................. H01L 41/08
[52] U.S. Cl. .................................. 310/311; 310/321; 310/328; 73/23; 73/61 R; 422/56; 422/57; 435/4; 435/29; 436/827; 436/828; 436/829
[58] Field of Search .................. 310/311, 312, 313 R, 310/321, 323, 324, 363, 364; 73/23, 24, 28–30, 61 R, 61.1 R, 61.2; 435/4, 7, 23, 29, 32, 34, 38–40; 422/98, 56, 57; 436/828, 52, 86, 95, 148, 532–535, 819, 827, 829; 23/293 R

[56] References Cited

U.S. PATENT DOCUMENTS

| 3,200,271 | 8/1965 | Haines | 310/328 |
| 3,260,104 | 7/1966 | King, Jr. | 73/23 |
| 3,266,291 | 8/1966 | King, Jr. | 73/23 |
| 3,343,044 | 9/1967 | King, Jr. et al. | 310/328 X |
| 3,561,253 | 2/1971 | Dorman | 310/328 X |
| 3,879,992 | 4/1975 | Bartera | 310/321 X |
| 4,210,722 | 7/1980 | Silver | 310/311 X |
| 4,236,893 | 12/1980 | Rice | 310/312 |
| 4,242,096 | 12/1980 | Oliveria et al. | 310/312 X |
| 4,246,344 | 1/1981 | Silver, III | 310/311 X |
| 4,314,821 | 2/1982 | Rice | 310/312 X |
| 4,598,224 | 7/1986 | Ballato | 310/311 |

FOREIGN PATENT DOCUMENTS

0631811 11/1978 U.S.S.R. .................................. 310/328

*Primary Examiner*—Mark O. Budd
*Attorney, Agent, or Firm*—Bruce L. Adams; Van C. Wilks

[57] ABSTRACT

A bio-sensor is mounted in a container and comprised of a receptor for selectively reacting with a specific biochemical substance in a sample liquid held in the container to bind thereon the specific biochemical substance and a resonator integrated with the receptor for detecting the amount of the specific biochemical substance bound to the receptor in terms of a resonant frequency shift of the resonator. A measuring circuit is connected to the sensor for measuring the resonant frequency shift of the resonator within the container; a switching valve operates during the reaction of the receptor with the specific biochemical substance to charge a sample liquid into the container to contact the sample liquid with the receptor to thereby effect the reaction and operates during the measurement of the resonant frequency shift to replace the sample liquid by a buffer liquid in the container to immerse the sensor in the buffer liquid to thereby prevent a fluctuation of the resonant frequency shift.

52 Claims, 9 Drawing Sheets

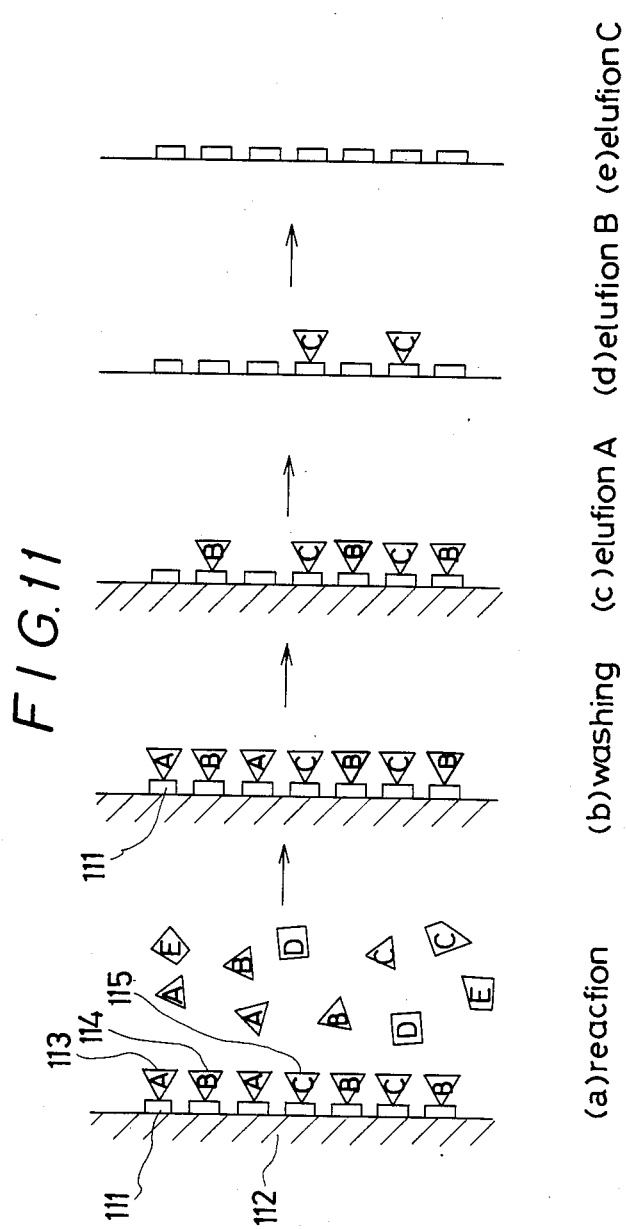

ANALYTICAL DEVICE AND METHOD UTILIZING A PIEZOELECTRIC CRYSTAL BIOSENSOR

BACKGROUND OF THE INVENTION

1. Field of the Invention

The present invention relates to an analytical device and a method for the analysis of biochemicals, microbes and cells utilizing a piezoelectric crystal biosensor.

2. Description of the Prior Art

Various methods for the determination of biochemicals, microbes and cells have included liquid chromatography, electrophoresis, direct observation of agglutination with the naked eyes, and other analytical methods, applying amplification with enzymes, fluorescence chemicals and radio isotopes (EIA, FIA, RIA).

Particularly, for the detection a pathogenic microorganism, a conventional method is comprised adding an antibody solution drop to a microbial suspension and observing the agglutination with the naked eye by using an agglutination plate. Recently, a system for the judgement of the agglutination has been developed, employing an image processing system equipped with a microscope. Further, a method applied to electrochemical determination and immuno reaction has been known. In this method, a microorganism is bound to an antibody immobilized on an organic film and the aimed concentration thereof is determined by measuring a change in the membrane potential.

On the other hand, for immunoassay, a surface acoustic wave (SAW) device has been developed, and one saw device is reported in the following document: J. E. Roederer and G. J. Bastiaans, Anal. Chem. 1983, 55, 2333-2336. This reference discloses that the determination of human IgG is carried out by promoting specific adsorption between immobilized goat anti-human IgG and human IgG at the surface of SAW device. The problem in the above methods, especially in agultination methods, are that the aggultination judged with the naked eye requires those skilled in the art. In addition, these methods give a poor quantitative result and can be hardly automated.

Furthermore, these conventional methods have some disadvantages in that they give poor sensitivity and require troublesome operation.

The image processing system has a large scale and requires considerable cost. The method, utilizing membrane potential, requires troublesome operations and can be hardly automated.

The other methods, for the immunoassay such as EIA, FIA and RIA, although they have a good sensitivity, require, also, troublesome operations.

The SAW device, for human IgG, only has a roughly determination range of human IgG: 0.0225-2.25 mg/ml.

SUMMARY OF THE INVENTION

The present invention has made it possible to detect biochemical substances such as biochemicals, microbes and cells and to determine the concentration of the same by the method of immobilizing biochemicals or organic compounds on the surface of the electrode of piezoelectric crystal to modify the surface, specifically conducting binding reaction of the biochemicals or organic compounds with biochemicals to cause weight change on the electrode surface of piezoelectric crystal, and measuring the resonant frequency change induced by the weight change.

It is, therefore, an object of the present invention to provide a piezoelectric crystal biosensor, which can detect biochemicals microbes and cells, in particular pathogenic microorganisms, and to selectively determine the concentration of the same.

Another object of the invention is to provide high sensitive determination method for the piezoelectric crystal biosensor.

A further object of the invention is to provide an improved piezoelectric crystal biosensor, which can analyze the constituents of biochemicals.

In accordance with the method of the present invention, the measuring system utilizing a piezoelectric crystal biosensor has high sensitivity and short operation time. This method has merits such as inexpensive cost automatical operation and repeated analysis.

The above and further objects and novel features of the invention will more fully appear from the following detailed description when the same is read in connection with the accompanying drawings. It is to be expressly understood, however, that the drawings are for purpose of illustration only and is not intended as a definition of the limits of the invention.

BRIEF DESCRIPTION OF THE DRAWINGS

FIG. 11 shows the principle of example 5;

FIG. 12(*b*) is a graph showing the relation between each pH of buffer solution and the difference of the resonant frequency;

DETAILED DESCRIPTION OF THE INVENTION

Figure 1:
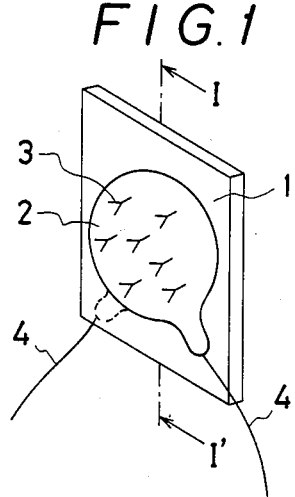
FIG. 1 is a perspective view of the entire construction of the piezoelectric crystal biosensor.

I. Piezoelectric crystal biosensor for the detection of a pathogenic microbe The present invention has made it possible to detect a microorganism, in particular a pathogenic one, and to determine the concentration of the same by immobilizing an antibody on the surface of a piezoelectric crystal biosensor, specifically binding the antibody to a microorganism to thereby cause a weight change on the surface of electrodes of the piezoelectric crystal biosensor, and measuring the change or shift in the resonant frequency of the piezoelectric crystal biosensor induced by the above weight change.

The amount of microorganisms bound to an immobilized antigen through an antigen-antibody reaction in a definite time, depends on the concentration of the microorganism. Thus the resonant frequency change of the piezoelectric crystal biosensor depends on the concentration of the microorganism.

The piezoelectric crystal of a known resonant frequency is immersed in a microbial suspension or sample liquid to thereby promote an antigen-antibody reaction, and then the resonant frequency is measured again. Thus the concentration of the microorganism can be determined from the resonant frequency change based on a calibration curve which is previously obtained.

Accordingly, the piezoelectric crystal biosensor of the present invention has made it possible to detect a microorganism and to determine the concentration of the same.

EXAMPLE 1

Referring to the drawings, a piezoelectric crystal biosensor for determination of Candida (*Candida albicans* (hereinafter referred to as *C. albicans*)) which is a pathogenic yeast, will be described in detail as an embodiment of the piezoelectric crystal biosensor of the present invention.

Figure 2:
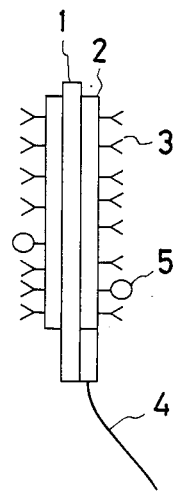
FIG. 2 is a sectional view of the piezoelectric crystal biosensor taken along line I-I' of FIG. 1.
Figure 3:
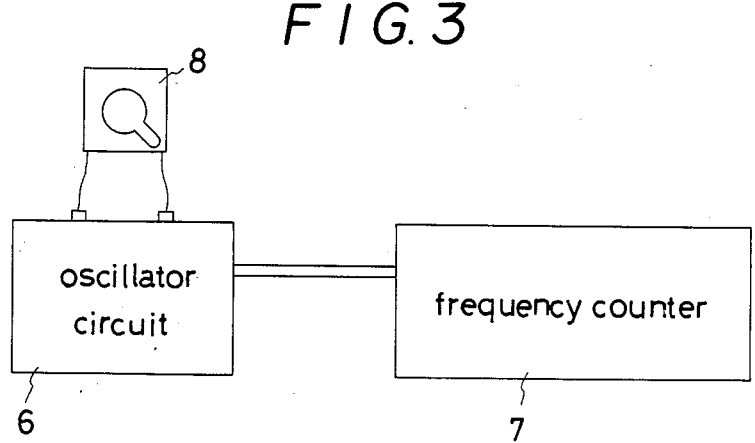
FIG. 3 is a block diagram of the measurement system for the piezoelectric crystal biosensor.

FIG. 1 is a perspective view of the piezoelectric crystal biosensor. In FIG. 1, a pair of electrodes 2 on which *C. albicans* antibody 3 was immobilized were provided on the opposite sides of a resonator in the form of a piezoelectric crystal 1. These electrodes 2 were connected with an oscillator circuit 6 through lead wires 4 as shown in FIG. 3. An AT-cut piezoelectric crystal of 9 MHz was employed as the resonator. FIG. 2 is a sectional view of the piezoelectric crystal biosensor taken along line I—I' of FIG. 1, wherein 5 is *C. albicans* captured by or found to the Candida antibody. In these figures, the antibody 3 and the yeast 5 are extremely enlarged.

The *C. albicans* antibody was immobilized to form a receptor on the surface of the electrodes in the following manner. The surface of each electrode 2 of the piezoelectric crystal 1 was plated with palladium and thereafter the electrode 2 was electrolytically oxidized. After treating the piezoelectric crystal in 2% solution of γ-aminopropyl triethoxy silane in acetone for an hour, washing the same with water and drying, the resonant frequency $F_1$ was measured. The measurement was performed by connecting the lead wires 4 to the oscillator circuit 6 with the use of the frequency counter 7. Subsequently, the piezoelectric crystal was treated to in 5% aqueous solution of glytaraldehyde for three hours and *C. albicans* antibody was added dropwise on the electrodes and allowed to stand for 30 minutes to thereby immobilize the antibody on the electrodes. Then the unreacted aldehyde groups were treated with 0.1M glycine for 30 min.

Figure 4:
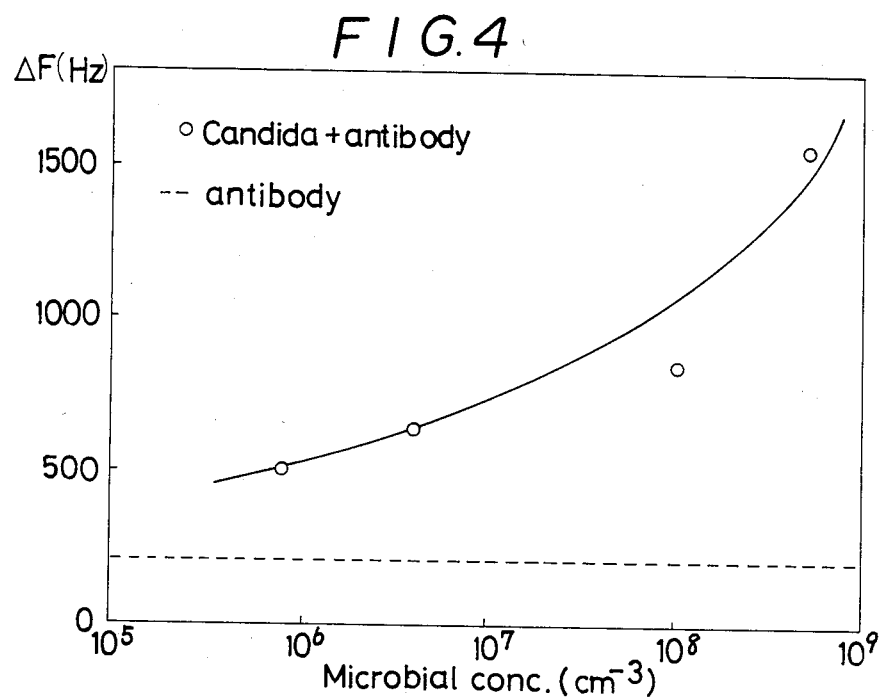
FIG. 4 is a graph showing the correlation of Candida (*C. albicans*) concentration and frequency change of the piezoelectric crystal biosensor.

The piezoelectric crystal biosensor 8 for the determination of *C. albicans* thus formed was operated as follows. This sensor was washed with 0.5M NaCl solution and immersed in *C. albicans* sample solution or liquid. After allowing the sensor to stand for 30 minutes, the sensor was washed with 0.5M NaCl solution again and the resonant frequency $F_2$ was measured. FIG. 4 shows the relationship between the resonant frequency and the *C. albicans* concentration, wherein the abscissa refers to the concentration of *C. albicans* while the ordinate refers to the frequency change ($\Delta F = F_1 - F_2$). This plot is formed by measuring $F_2$ with the use of sample liquids of various *C. albicans* concentrations. Each microbial concentration is measured with a hemocytometer. In FIG. 4, each mark O represents a measured value. FIG. 4 indicates that the resonant frequency or shift change, $\Delta F$, increases depending on the microbial concentration. In FIG. 4, the dotted line represents a resonant frequency change caused by the antibody alone.

Figure 5:
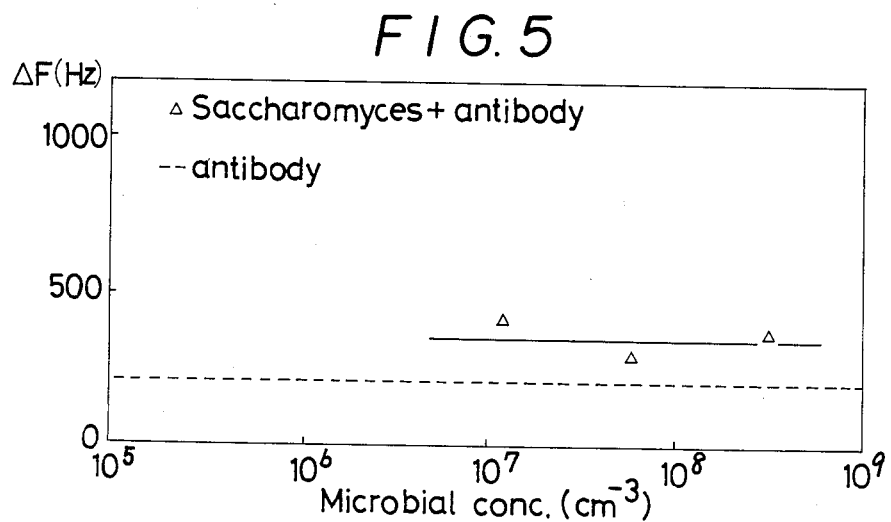
FIG. 5 is a graph showing the correlation of Saccharomyces (*S. cerevisiae*) concentration and frequency change of the piezoelectric crystal biosensor.

FIG. 5 shows a plot of $\Delta F$ relative to the microbial concentration of solutions of Saccharomyces (*Saccharomyces cerevisiae* (hereinafter referred to as *S. cerevisiae*)), which is also a yeast, measured in the same manner as the one described above with the piezoelectric crystal biosensor for *C. albicans* of the present invention. FIG. 5 suggests that the frequency shows no change depending on the *S. cerevisiae* concentration. Further examinations on *Escherichia coli* and Bacillus are carried out. Consequently, it is found that no change in the frequency is observed in these cases similar to the case of *S. cerevisiae*. Thus the piezoelectric crystal biosensor for *C. albicans* of the present invention has an excellent selectivity or specificity.

As a result of an examination on a mixture of *C. albicans* with *S. cerevisiae*, it is found that the change in he frequency depends on the concentration of *C. albicans* alone.

II. Piezoelectric crystal biosensor for determination of biochemicals

The inventors have succeeded in determining the concentration of biochemicals with a high accuracy by utilizing a piezoelectric crystal biosensor, wherein an antibody or an antigen is immobilized on the surface of each electrode and the biosensor is mounted in a container in the form of a flow type cell. In the piezoelectric crystal biosensor system of the present invention, the piezoelectric crystal biosensor is incorporated in a flow type cell to thereby handle the sensor in a liquid at any time. To avoid unstable oscillation or fluctuation of the resonant frequency caused by mechanical pressure, the piezoelectric crystal is immersed in water as a whole. Further, since the resonant frequency of the oscillator varies depending on the temperature, conductivity and flow rate of the liquid, the measurements of the frequency before and after the antigen-antibody reaction are carried out by replacing the sample liquid with distilled water and feeding the distilled water maintained at a given temperature in a thermostatic bath to the cell at a constant rate.

Further, the inventors have succeeded in enhancing the sensitivity of a piezoelectric crystal biosensor. After all antibody or antigen is immobilized on the surface of each electrode of the piezoelectric crystal, latexes or other fine particles, on which an antibody or an antigen is immobilized, via antigen-antibody reaction to a substrate, is bound via antigen-antibody reaction with the immobilized antibody or antigen on the piezoelectric crystal.

In the determination with the piezoelectric crystal biosensor according to the present invention, the weight change of the surface of the piezoelectric crystal is amplified with latexes or other fine particles.

EXAMPLE 2

The piezoelectric crystal biosensor was prepared in the following procedure. The surface of each electrode of the piezoelectric crystal was plated with palladium and anodized in 0.5M NaOH for one hour. Then it was treated in 10% γ-amino propyl triethoxy silane in acetone for two hours and then in 5% glutaraldehyde aldehyde for three hours. Subsequently, it was immersed in 1 mg/ml solution of protein A for formimg a receptor to be immobilized. It was further immersed in 0.1M glycine for 30 minutes to remove unreacted aldehyde groups.

Figure 6:
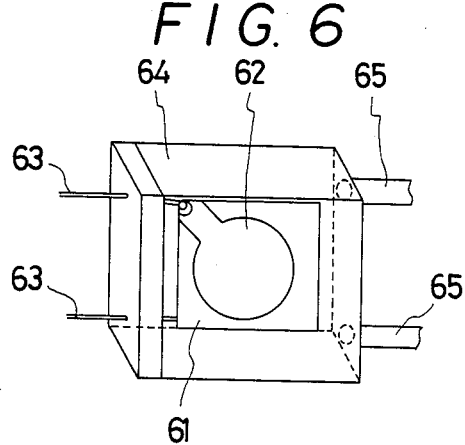
FIG. 6 is a perspective view of a biosensor and a cell.
Figure 7:
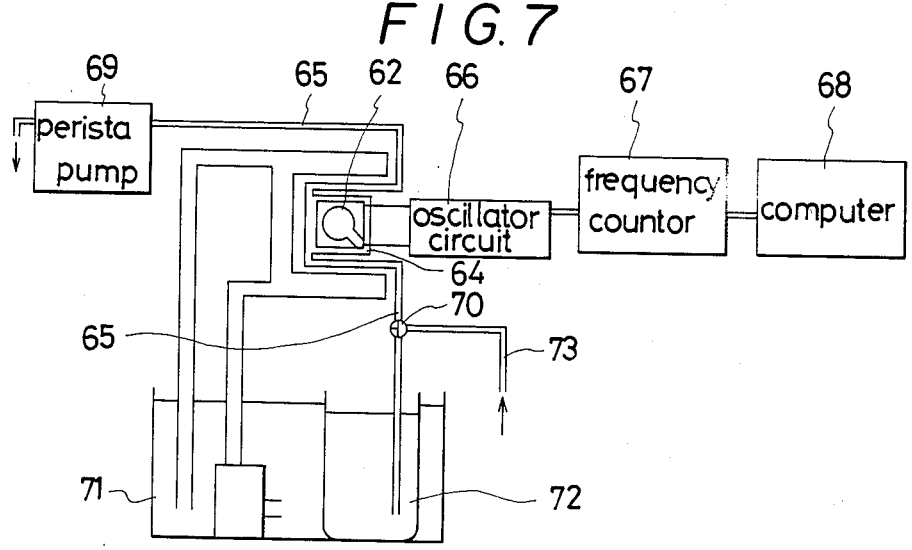
FIG. 7 is a block diagram of the entire biosensor system.

The determination in this example was performed according to a flow system as shown in FIG. 7. FIG. 6 shows a biosenor and a container or cell while FIG. 7 shows the entire system. In FIG. 6, an electrode 62 on which the receptor is immobilized in the above-mentioned procedure was provided on each side of a piezoelectric crystal 61. Each electrode is connected to a lead wire 63. A cell 64 is placed in such a manner as to accommodate therein the piezoelectric crystal 61. Pipes 65 are provided in the cell to circulate liquid therein. The lead wires 63 are drawn outside the cell 64 and connected to an oscillator circuit 66 as shown in FIG. 7. The oscillator circuit 66 is connected to a frequency counter 67 to which a computer 68 is connected to process the data obtained by the frequency counter 67. One of the pipes or outlet 65 connected to the cell 64 placed around the piezoelectric crystal 61 is connected to a pump 69 to pass or circulate the liquid through the cell 64, while the other pipe or inlet 65 is connected to an outlet of a three-way valve 70. One inlet of the three-way valve 70 is selectively switched to open for introducing into the cell 64 distilled water 72 stored in a thermostatic bath 71 and another inlet 73 is selectively switched to open for introducing 0.5M NaCl and glycine-hydrochloride buffer solution (pH 2.8) and sample solutions.

The determination of human IgG with the piezoelectric crystal biosensor system was carried out in the following manner. A glycine-hydrochloride buffer solution (pH 2.8) was circulated through the cell to remove adsorbates. Then the content of the cell was replaced by distilled water and the oscillation frequency $F_1$ was measured while feeding the distilled water at the constant rate. The resonant frequency was monitored continuously until the frequency become constant. Then human IgG solution was circulated through the cell and allowed to react with the receptor for 30 minutes at 30° C. Then a solvent liquid in the form of 0.5M NaCl was circulated therethrough to remove non-specific adsorbates or substances attached to the receptor. The content of the cell was replaced with distilled water again and the oscillation frequency $F_2$ was measured while feeding the distilled water at a constant rate. Then another solvent liquid in the form of glycine-hydrochloride buffer solution (pH 2.8) was circulated through the cell to thereby remove the specific adsorbate for rinse.

Figure 8:
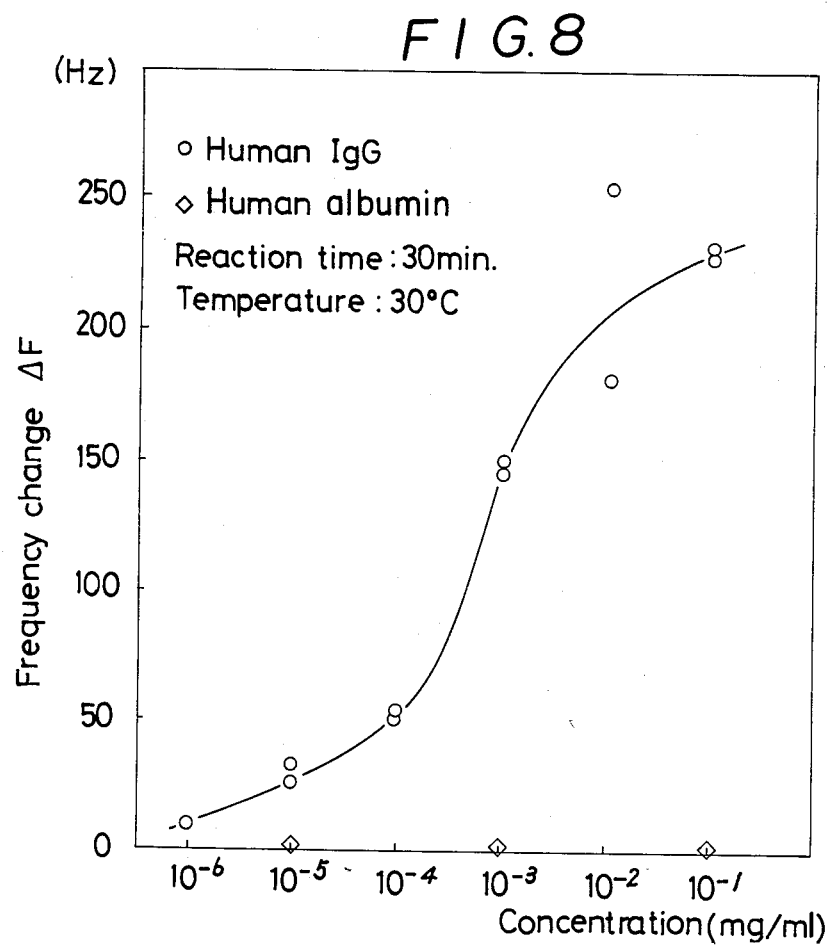
FIG. 8 is a graph showing the correlation of human IgG concentration and frequency change.

FIG. 8 shows a relationship between the human IgG concentration and the resonant frequency change of the piezoelectric crystal biosensor on which protein A is integrated as the receptor. The ordinate refers to the resonant frequency change ($\Delta F = F_1 - F_2$) while the abscissa refers to human IgG concentration. Thus it is found that the frequency varies depending on human IgG concentration.

It is further found that the frequency returns to the original value after circulating the buffer solution (pH 2.8) through the cell and that the frequency further varies by an additional reaction and the sensor is used over ten times. As a result of an examination on human albumin, no response is obtained, which suggests that this system responds specifically to IgG. A similar result is obtained when the anti-human IgG antibody is employed.

EXAMPLE 3

Referring to the drawings, an application of the present invention to the determination of human IgG will be described in detail.

Figure 9:
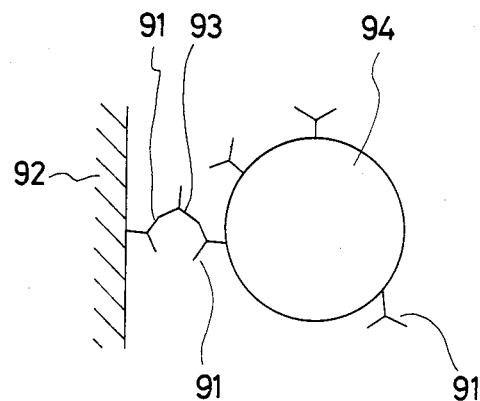
FIG. 9 and FIG. 10 show the principle of examples 3 and 4, respectively.

FIG. 9 shows the principle of the present arrangement, wherein numeral 91 is anti-human IgG antibody immobilized on an electrode 92 of a piezoelectric crystal, 93 is human IgG which is a sample substrate and 94 is a fine article in the form of a latex on which anti-human IgG antibody 91 is immobilized in order to enhance the sensitivity.

The piezoelectric crystal biosensor was prepared in the same procedure as the one described in Example 2 except that anti-human IgG was immobilized on the biosensor. The same determination system as that used in Example 2 was employed.

In the above structure, glycine-hydrochloride buffer solution (pH 2.8) was introduced into the cell to remove adsorbates. Then the content of the cell was replaced with liquid in the form of distilled water and the resonant frequency $F_1$ was measured at a constant flow rate of distilled water. Subsequently, human IgG solution was introduced into the cell and allowed to react with the receptor for 30 minutes at 30° C. in the cell.

0.5M NaCl was circulated through the cell to remove non-specific adsorbates. Then the resonant frequency $F_2$ was measured again. Further latexes on which anti-human IgG antibody was immobilized were introduced into the cell and allowed to react with human IgG bound to the receptor for 30 minutes. After passing 0.5M NaCl through the cell again, the resonant frequency $F_3$ was measured. Table 1 shows the frequency shift in response to the binding of IgG ($F_1 - F_2$) and that enhanced by the latexes ($F_1 - F_3$). Table 1 suggests that these latexes can enhance the sensitivity.

TABLE 1

| Human IgG conc. (mg/ml) | $F_1-F_2$ (Hz) | $F_1-F_3$ (Hz) |
| --- | --- | --- |
| $1 \times 10^{-4}$ | 26 | 51 |

EXAMPLE 4

Referring to the drawings, an application of the present invention to the determination of human IgG will be described in detail.

Figure 10:
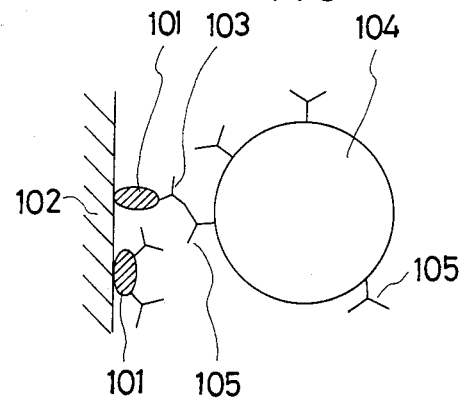

FIG. 10 shows the principle of the present arrangement, wherein numeral 101 is protein A immobilized on the surface of an electrode 102 of a piezoelectric crystal, 103 is human IgG which is a sample substrate and 104 is a latex on which anti-human IgG antibody 105 (mouse $IgG_1$) is immobilized in order to enhance the sensitivity.

The piezoelectric crystal biosensor was prepared in the same procedure as that described in Example 2. The same determination system as that used in Application 2 was employed.

In the above structure, glycine-hydrochloride buffer solution (pH 2.8) was introduced into the cell to remove adsorbates. Then the content of the cell was replaced with distilled water and the resonant frequency $F_1$ was measured at a constant flow rate of distilled water. Subsequently, human IgG solution was introduced into the cell and allowed to react with the receptor for 30 minutes in the cell. 0.5M NaCl was circulated through the cell to remove non-specific adsorbates. After replacing the content of the cell with distilled water, the resonant frequency $F_2$ was measured again. Further latexes, on which anti-human IgG antibody (mouse $IgG_1$) was immobilized, were introduced into the cell and allowed to react with the bound IgG for 30 minutes. After introducing phosphate buffer solution (pH 6) into the cell to thereby remove latexes directly bound to protein A, the content of the cell was replaced with distilled water and the resonant frequency $F_3$ was measured.

Comparing the obtained response upon human IgG, i.e., $\Delta F_{1-2}$ ($F_1-F_2$) with the one enhanced with the latexes, i.e., $\Delta F_{1-3}$ ($F_1-F_3$), it was found that $\Delta F_{1-3}$ exhibited an enhanced response proportional to $\Delta F_{1-2}$. This fact suggests that the latexes, on which anti-human IgG is immobilized, can enhance the sensitivity.

III. Application to analysis of biochemicals

The constituents or species of particular biochemical are analyzed by the steps of immobilizing materials exhibiting different adsorptivities upon various biochemicals on the surface of a piezoelectric crystal, successively introducing eluents different in properties through the cell and determining change in the resonant frequency before and after the elution.

Namely, a sample to be analyzed is previously adsorbed on the surface of the piezoelectric crystal biosensor on which a receptor selected from enzymes, sugars, lipids, co-enzymes, amino acids and proteins such as lectins antibodies or protein A, is immobilized and then the constituents of the sample are eluted with eluents slightly different in pH value or ionic strength from each other or containing organic solvents. Thus the presence and amount of each constituent can be determined from the resonant frequency change of the piezoelectric crystal biosensor before and after the elution.

The constituents of biochemicals can be analyzed with the use of a piezoelectric crystal biosensor by taking advantage of the specificity of adsorbent with respect to materials immobilized on the surface of the piezoelectric crystal to adsorb various substances. This sensor has wide application by selecting proper materials to be immobilized on the surface and eluents.

EXAMPLE 5

Referring to the drawings, an application of the present invention to the analysis of mouse $\gamma$-globulin will be described in detail.

FIG. 11 shows the principle of the present arrangement wherein numeral 111 is protein A immobilized on the surface of an electrode 112 of a piezoelectric crystal and 113, 114 and 115 are, respectively, mouse $IgG_1$, $IgG_{2a}$ and $IgG_{2b}$ to be analyzed. As shown in FIg. 11(a), immobilized protein A reacted with mouse IgG and was rinsed (FIG. 11(b)). Then the resonant frequency $F_0$ (Hz) was measured. Subsequently $IgG_1$ 113 was eluted with an eluent A and the resonant frequency $F_1$ (Hz) was measured again. Thus the amount of $IgG_1$ 113 was determined by a change in the resonant frequency, i.e., $F_1-F_0$. The amounts of $IgG_{2a}$ 114 and $IgG_{2b}$ 115 can be determined in the same procedure.

The piezoelectric crystal biosensor was prepared in the same procedure as that described in example 2. The determination in this example was performed according to a flow system as shown in FIG. 7.

In the system as shown in FIG. 7, a glycine-hydrochloride buffer solution (pH 2.8) was introduced into the cell to remove adsorbates. Then the content of the cell was replaced with distilled water and the resonant frequency was measured in a constant flow of distilled water. Subsequently, 0.1 mg/ml mouse $\gamma$-globulin solution in phosphate buffer solution (pH 8) was introduced into the cell and allowed to react with the reaction for 30 minutes while maintaining the cell at 30° C.

Figure 12A:
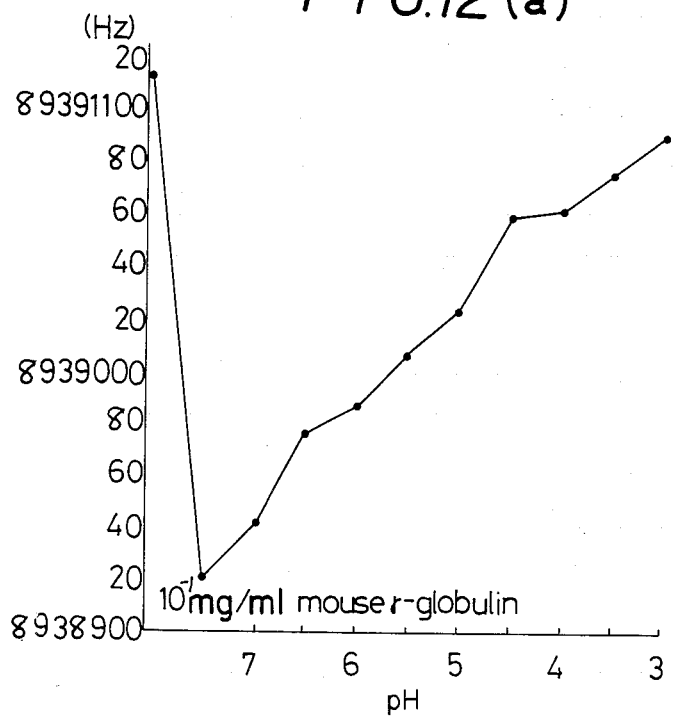
FIG. 12(*a*) is a graph showing the resonant frequency before and after the reaction with mouse γ-globulin.
Figure 12B:
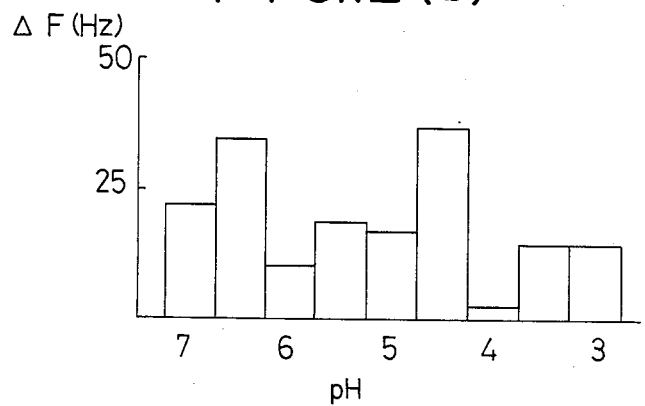

Then the content of the cell was replaced with distilled water and the resonant frequency was measured. Subsequently, it was successively eluted with phosphate/citrate buffer solutions of pH 7.0, 6.5, 6.0, 5.5, 5.0, 4.5, 4.0, 3.5 and 3.0 and the resonant freqency was measured followed by each elution. FIG. 12(a) shows the resonant frequency change thus measured. FIG. 12(b) is a graph which shows the difference in the resonant frequencies measured before and after each elution obtained from the result in FIG. 12(a). FIG. 12(b) suggests that there are three obvious peaks.

These peaks correspond to $IgG_1$, $IgG_{2a}$ and $IgG_{2b}$, respectively. This result well conforms with that obtained by affinity chromatography with the use of protein A immobilized gel column, P.L. Ey et al Immunochemistry, 15 (1978) 429.

EXAMPLE 6

Figure 13:
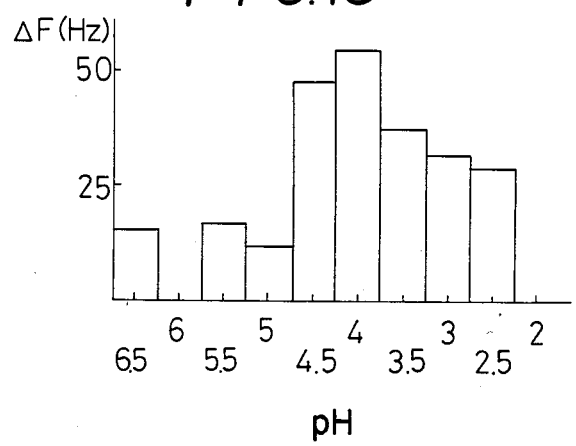
FIG. 13 shows difference of the resonant frequency for the analysis of the constituents of human IgG.

The constituents of human IgG were analyzed in the same system and in the same manner as those described in Example 2. Namely, a piezoelectric crystal biosensor on which protein A was immobilized was used as in Example 2. Similar to Example 2, glycine hydrochloride buffer solution (pH 2.8) was introduced into the cell to thereby remove adsorbates. Then the content of the cell was replaced with distilled water and the resonant frequency was measured in a constant flow of distilled water. Subsequently, 0.1 mg/ml solution of human $\gamma$-globulin in phosphate buffer solution (pH 7) was introduced into the cell and allowed to react with the receptor for 30 minutes while maintaining the cell to 30° C. Then the content of the cell was replaced with distilled water and the resonant frequency was measured. Subsequently each of the human $\gamma$-globulin species was successively eluted with phosphate-citrate buffer solutions of pH 6.5, 6.0, 5.5, 5.0, 4.5, 4.0, 3.5, 3.0 and 2.5 and the resonant frequency was measured after each solution. FIG. 13 is a graph of the resonant frequencies difference before and after the elution determined from a change in the resonant frequency. This result shows a similar tendency to that reported by R. C. Duhamel, P. H. Schur and K. Brendel (cf. J. Immunol. Methods, 31, 211 (1979)), i.e., showing the elution of $IgG_2$ and $IgG_4$ at around pH 4.7 and the elution of $IgG_1$ and $IgG_4$ at around pH 4.3.

In this application, protein A alone was employed as a material which can adsorb biochemicals, furthermore, two or more materials, which can adsorb the biochemicals to be analyzed, may be immobilized. In such a case, each biochemical may be analyzed by selecting appropriate eluents by taking advantage of the difference in the ability of the materials immobilized on the surface of the piezoelectric crystal to adsorb the biochemicals to be analyzed.

IV. Analysis of biochemicals, microorganisms or cells by using a plurality of piezoelectric crystal biosensors A plurality of biochemicals can be analyzed by an analytical system equipped with a plurality of piezoelectric crystal biosensors each having a different material immobilized or chemically treated on its surface. Further the analysis can be accelerated by measuring the referential piezoelectric crystal employing in non-stationary state and measuring the difference between the resonant frequency of referential piezoelectric crystal and the resonant frequencies of piezoelectric crystal biosensors.

Namely, the analysis can be accelerated by using an analytical system wherein piezoelectric crystals on which no material is immobilized are used as referential sensors, which can remove deviations effect of short-period aging and changes in the conductivity and temperature of the sample solution.

EXAMPLE 7

Referring to the drawings, an application of the present invention to an ABO blood type sensor will be described in detail.

Figure 14:
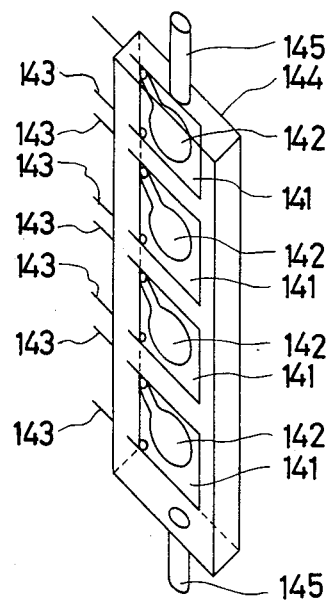
FIG. 14 is a perspective view of AT-cut piezoelectric crystals and a cell for use in the analysis of biochemicals.
Figure 15:
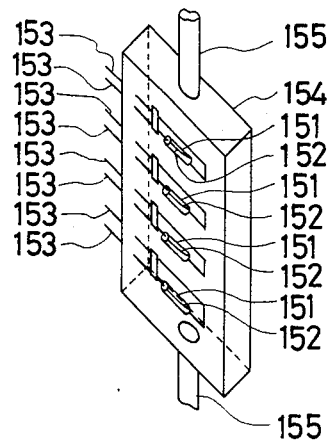
FIG. 15 is a perspective view of GT-cut piezoelectric crystals and a cell for use in the analysis of biochemicals.

FIG. 14 is a perspective view of a piezoelectric crystal biosensor and a cell. Piezoelectric crystals of AT-cut 9 MHz are employed. An electrode 142 is provided on each side of each piezoelectric crystal 141 and a lead 143 is connected thereto. A cell 144 is placed in such a manner as to accommodate therein piezoelectric crystals 141. A pipe 145 is provided in the cell 144 to thereby circulate a liquid therethrough. The leads 143 are drawn outside the cell 144. FIG. 15 is a perspective view of a piezoelectric crystal biosensor equipped with piezoelectric crystals 151 of GT-cut 4 MHz and a cell. On three piezoelectric crystals, *Phaseolus Limensis Agglutinin, Bandeiraea Simplicifolia Lectin I* and *Ulex Europaeus Agglutinin I* are immobilized, respectively.

Figure 16:
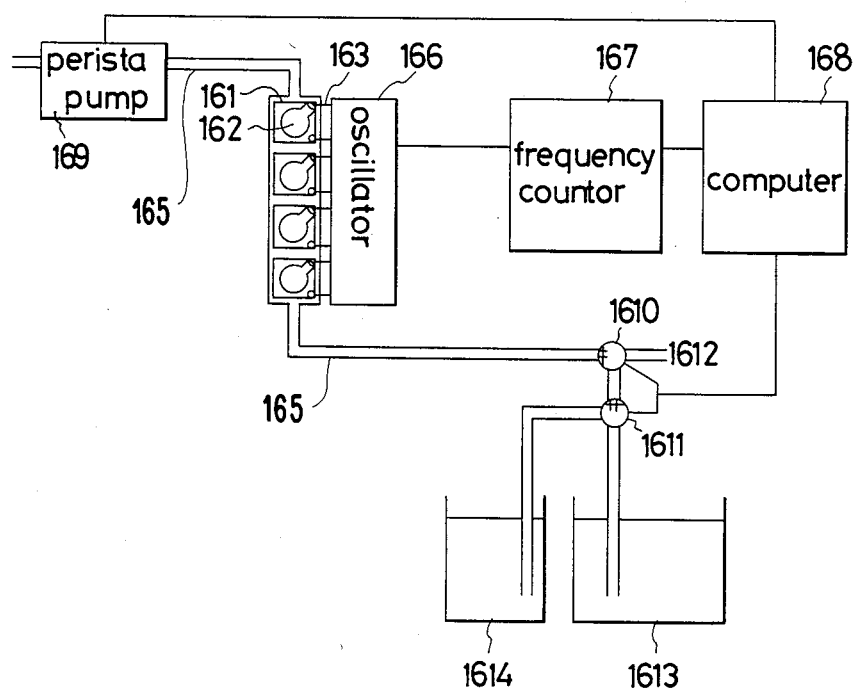
FIG. 16 is a block diagram of the determination system for multi analysis.

FIG. 16 is a block diagram of the determination system for biochemicals with the use of piezoelectric crystal biosensors. A lead 163 drawn from an electrode 162 provided on the surface of a piezoelectric crystal 161 is connected to a oscillator circuit 166 which is connected to a frequency counter 167.

One end of a pipe provided in a cell disposed around the piezoelectric crystal 1 is connected to a pump 169 to thereby circulate liquid through the cell. The other end of the pipe is connected to the outlet of a solenoid valve 1610. The inlets of the solenoid valve are mounted to another solenoid valve 1611 and a sample inlet 1612. The inlets of the solenoid valve 1611 are connected to a reservoir 1613 of 0.05M phosphate buffer solution (pH 7.5) and a reservoir 1614 of 0.1M α-L-fucose and 0.1M N-acetyl-D-glucosamine. The frequency counter 167, peristalic pump 169 and solenoid valves 1610 and 1611 are connected to a computer 168 by which the determination system is controlled.

The piezoelectric crystal was prepared in the following manner. The surface of each electrode of the piezoelectric crystal was plated with palladium and treated anodically to oxidize in 0.5M NaOH for one hour.

Then it was treated in and acetone solution containing 5% trisyl chloride and 1.2% pyridine for 30 minutes and washed with 5 mM HCl. Each lectin was immobilized by immersing the piezoelectric crystal in 1 mg/ml lectin solution for one hour. It was further treated in 0.1M glycine solution for 30 minutes to thereby remove unreacted aldehyde groups.

ABO blood type judgement by this device was carried out in the following procedure.

Three piezoelectric crystals each having a lectin immobilized thereon and a referential piezoelectric crystal were previously resonated in a cell through which buffer solution was passed. Then the solenoid valve 1610 was switched to thereby introduce blood cell sample via the sample inlet 1612. The sample was arbitrarily diluted by adjusting the solenoid valve 1610. When the sample was passed through the cell, the peristalic pump 169 was controlled so as to maintain a low flow rate to thereby secure sufficient progress of the reaction. Then phosphate buffer pH 7 was passed through the cell to remove non-specific adsorbates. The resonant frequency of each piezoelectric crystal was measured. The differences of the resonant frequency between each of the piezoelectric crystals on which one of the three lectins was, respectively, immobilized and the referential piezoelectric crystal was measured. Thus the blood type was judged depending on a change in the data determined before and after the reaction with the sample.

As a result, it was found that the piezoelectric crystal on which *Phaseolus Limensis Agglutinin* was immobilized responded to erythrocytes having type A factor alone. On the other hand, the one on which Bandeiraea Simplicifolia Lectin I was immobilized responded to both of type A and type B factors but show higher response to the latter. Thus the blood types of A, B and AB can be distinguished from each other by comparing the responses by the pieozoelectric crystal on which *Phaseolus Limensis Agglutinin* was immobilized. In contrast, the piezoelectric crystal on which *Ulex Europaeus Agglutinin I* was immobilized responded to type O erythrochtes alone.

Then the solenoid valve 11 was switched to thereby introduce 0.1M α-L-fucose and 0.1M N-acetyl-D-glucosamine (pH 7.5) into the cell. Thus erythrocytes bound to the surface of the lectins were removed. Subsequently a sufficient amount of phosphate buffer (pH 7.5) was introduced and the determination was performed again.

As described before, the analytical device of the present invention can accelerate continuous judgement of ABO blood types. Further a smaller cell can be used in a device wherein GT-cut piezoelectric crystals are employed, which brings about an additional advantage that only a smaller amount of a sample is required.

While the inventors have shown and described particular embodiments of our invention, it will be obvious to those skilled in the art that various changes and modifications may be made without departing from our invention in its broader aspects and we, therefore, intend in the appended claims to cover all such changes and modifications as full within the true spirit and scope of our invention.

What is claimed is:

1. A device for analyzing biochemicals, microbes and cells in a sample liquid comprising: a flow type cell for containing therein a sample liquid; a piezoelectric crystal sensor incorporated in the flow type cell, the piezoelectric crystal sensor having a piezoelectric crystal and receptor material immobilized or chemically treated on a surface of the piezoelectric crystal, the receptor material being operative to attach thereto a biochemical, microbe or cell specific for the receptor material; measuring means for measuring the resonant frequency of the piezoelectric crystal to analyze the biochemical, microbe or cell attached to the receptor material; and replacing means for replacing the sample liquid in the flow type cell by water held at a substantially constant temperature so that the resonant frequency is measured while the piezoelectric crystal is exposed to the water.

2. A device as claimed in claim 1; wherein the replacing means includes means for circulating distilled water through the flow type cell at a constant rate so that the measurement of the resonant frequency is carried out while circulating the distilled water at the constant rate.

3. A device as claimed in claim 1; wherein the receptor material is comprised of biochemicals or organic compounds.

4. A device as claimed in claim 3; wherein the biochemical of the receptor material is selected from the group consisting of sugars, lipids, co-enzymes, amino acids and proteins including enzymes, lectins, antitodies and protein A.

5. A device as claimed in claim 1; wherein the flow type cell has a dimension such that the whole piezoelectric crystal is immersed in a sample liquid and water contained in the flow type cell.

6. A device as claimed in claim 1; wherein said piezoelectric crystal exhibits a resonant frequency change due to a weight change on the surface of the piezoelectric crystal when the receptor material absorbs the biochemicals, microbes or cells to be analyzed.

7. A device as claimed in claim 1; wherein the measuring means comprises an oscillator circuit and a frequency counter.

8. A device as claimed in claim 1; wherein the flow type cell has pipes connected to effect the circulation of a sample liquid through the flow type cell.

9. A device as claimed in claim 1; including supplying means for supplying the flow type cell with a solution effective to remove absorbates non-specific for the receptor material from the receptor material.

10. A device as claimed in claim 1; including a plurality of piezoelectric crystal sensors incorporated in the flow type cell, at least one of the piezoelectric crystal sensors exhibiting a resonant frequency change caused by a weight change on the surface of the piezoelectric crystal due to the attaching of the biochemical, microbe or cell to the receptor material.

11. A device as claimed in claim 10; wherein at least two of the piezoelectric crystal sensors have different receptor materials immobilized or chemically treated on the surfaces of the piezoelectric crystals of the two piezoelectric crystal sensors.

12. A device as claimed in claim 10; wherein at least one piezoelectric crystal sensor has a piezoelectric crystal free from any receptor material.

13. A device as claimed in claim 11; wherein the different biochemical receptor materials are selected from the group consisting of sugars, lipids, co-enzymes, amino acids and proteins including enzymes, lectins, antibodies and protein A.

14. A method for the analysis of biochemicals, microbes and cells contained in a sample liquid using a piezoelectric crystal sensor which has a receptor material, comprising the steps of:

(a) measuring a resonant frequency $F_1$ of a piezoelectric crystal sensor within water held at a substantially constant temperature;

(b) contacting the piezoelectric crystal sensor with a sample liquid contained in a flow type cell and allowing a binding reaction of biochemicals, microbes or cells to be analyzed with a receptor material formed on the piezoelectric crystal sensor;

(c) flowing a solution into the flow type cell for removing substances bound to and non-specific for the receptor material from the receptor material;

(d) measuring a resonant frequency $F_2$ of the piezoelectric crystal sensor within water held at a substantially constant temperature; and (e) determining a concentration of the biochemicals, microbes or cells specific for the receptor material according to a frequency change $\Delta F = F_1 - F_2$ based on a calibration curve obtained previously.

15. A method according to claim 14; further comprising the step of flowing another solution into the flow type cell after the measurement of the resonant frequency $F_2$ for removing a substance bound to and specific for the receptor material from the receptor material to recover the piezoelectric crystal sensor.

16. A method according to claim 14; wherein the water comprises a distilled water.

17. A method according to claim 14; wherein the water is circulated at a constant rate to the flow type cell during the measurement of the resonant frequencies $F_1$ and $F_2$.

18. A method according to claim 14; wherein the solution used for removing substances non-specific for the receptor material comprises 0.5M NaCl solution.

19. A method according to claim 15; wherein the solution used for removing a substance specific for the receptor material comprises pH 2.4 glycine-HCl buffer solution.

20. A method according to claim 14; wherein the piezoelectric crystal sensor is modified with protein A to form thereon a receptor material.

21. A method according to claim 14; wherein Human IgG is analyzed by the piezoelectric crystal sensor.

22. A method according to claim 14; including the step of contacting the piezoelectric crystal sensor with a suspension of fine particles after removing substances non-specific for the receptor material from the receptor material so as to allow the fine particles to attach to a substance specific for and retained on the receptor material.

23. A method according to claim 22; further comprising the step of flowing a solution into the flow type cell for removing substances non-specific for the receptor material and contained in the suspension from the receptor material after contacting the piezoelectric crystal sensor with the suspension.

24. A method according to claim 22; wherein the fine particles are modified with biochemicals or organic compounds having an affinity to a substance specific for the receptor material.

25. A method according to claim 24; wherein the fine particles comprise a latex.

26. A method for the analysis of biochemicals, microbes and cells contained in a sample liquid utilizing a piezoelectric crystal sensor which has a receptor material, comprising the steps of:

(a) contacting the piezoelectric crystal sensor with a sample liquid contained in a flow type cell and allowing a binding reaction of different kinds of biochemicals, microbes or cells to be analyzed with a receptor material formed on the piezoelectric crystal sensor;

(b) measuring a resonant frequency of the piezoelectric crystal sensor in another liquid within the flow type cell;

(c) flowing an eluent into the flow type cell to selectively remove one kind of biochemicals, microbes or cells bound to the receptor material from the receptor material;

(d) measuring a resonant frequency of the piezoelectric crystal sensor in a buffer liquid within the flow type cell; and (e) determining an amount of the one kind of eluted biochemicals, microbes or cells according to the frequency difference of the measured resonant frequencies.

27. A method according to claim 26 including the steps of repeatedly flowing a different eluent into the flow type cell to successively remove a different kind of biochemicals, microbes or cells; and measuring resonant frequencies before and after the removal of a different kind of biochemicals, microbes or cells.

28. A method according to claim 27; wherein the eluent has a different pH or ionic strength, and contains materials which prevent the absorption or which contain organic solvents.

29. A method according to claim 26; wherein the measurement of the resonant frequencies is carried out when the piezoelectric crystal sensor is immersed in a distilled water within the flow type cell.

30. A method according to claim 29; wherein the water is circulated at a constant rate to the flow type cell.

31. A method according to claim 27; wherein Mouse IgG sub-classes are successively removed by different eluents to analyze Mouse IgG sub-classes.

32. An apparatus for analyzing biochemical substances contained in a sample liquid, comprising: a container for holding therein a liquid; a sensor mounted in the container and comprised of a receptor for selectively reacting with a specific biochemical substance in a sample liquid to bind thereon the specific biochemical substance, and a piezoelectric resonator integrated with the receptor for detecting the amount of the specific biochemical substance bound to the receptor in terms of a resonant frequency shift of the resonator; measuring means connected to the sensor for measuring the resonant frequency shift of the resonator within the container; and control means operative during the reaction of the receptor with the specific biochemical substance to charge a sample liquid into the container to contact the sample liquid with the receptor to thereby effect the reaction and operative during the measurement of the resonant frequency shift to replace the sample liquid with another liquid in the container to immerse the sensor in said another liquid to thereby prevent fluctuation of the resonant frequency shift.

33. An apparatus according to claim 32; wherein the container comprises a flow type cell having an inlet and outlet for charging and discharging a liquid into and from the cell.

34. An apparatus according to claim 33; wherein the control means includes valve means connected to the inlet of the flow type cell for selectively feeding the sample and another liquids to the flow type cell.

35. An apparatus according to claim 34; wherein the control means includes means for feeding said another liquid in the form of water held at a given temperature.

36. An apparatus according to claim 33; wherein the control means includes pump means connected to the flow type cell for circulating said another liquid at a constant rate through the flow type cell.

37. An apparatus according to claim 32; wherein the receptor has a receptive material effective to selectively react with a specific biochemical substance in the form of biochemicals, microbes and cells.

38. An apparatus according to claim 37; including a plurality of sensors, each sensor being comprised of a receptor having a different receptive material effective to selectively react with a different kind of a specific biochemical substance contained with the same sample liquid.

39. An apparatus according to claim 37; including a reference sensor free of a receptive material.

40. An apparatus according to claim 32; wherein the control means includes means for introducing a solvent liquid into the container effective to remove substances attached to and non-specific for the receptor prior to the measurement of the resonant frequency.

41. An apparatus according to claim 32; wherein the control means includes means for introducing a solvent liquid into the container effective to remove the specific substance bound to the receptor for recovering the sensor after the measurement of the resonant frequency.

42. A method for analyzing biochemical substances contained in a sample liquid by utilizing a sensor comprised of a receptor for selectively reacting with a specific biochemical substance to bind thereon the specific biochemical substance, and a piezoelectric resonator integrated with the receptor for converting the amount of the specific biochemical substance bound to the receptor into a resonant frequency shift thereof, the method comprising the steps of: mounting the sensor in a container; immersing the sensor in a liquid within the container; measuring an initial resonant frequency of the resonator of the sensor within the container; contacting the sensor with a sample liquid within the container to selectively bind a specific biochemical substance to a receptor of the sensor; replacing the sample liquid by another liquid within the container and immersing the sensor in the liquid; measuring a resultant resonant frequency of the sensor resonator; and determining the amount of the specific biochemical substance bound to the sensor receptor according to the resonant frequency shift between the initial and resultant resonant frequencies.

43. A method according to claim 42; including the step of exposing the sensor to a solvent liquid within the container after contacting the sensor to the sample liquid to thereby remove substances attached to and non-specific for the sensor receptor prior to the measurement of the resultant resonant frequency.

44. A method according to claim 42; including the step of exposing the sensor to a solvent liquid within the container after the measurement of the resultant resonant frequency to remove the specific biochemical substance bound to the sensor receptor to thereby recover the sensor.

45. A method according to claim 42; including the step of circulating a liquid through the container during the measurement of a resonant frequency of the sensor to prevent a fluctuation of a resonant frequency.

46. A method according to claim 45; wherein the step of circulating comprises calculating the liquid at a given rate in the form of water held at a given temperature.

47. A method according to claim 42; including the step of contacting the sensor with a suspension liquid containing suspended fine particles within the container after binding the specific biochemical substance to the sensor receptor to couple the suspended fine particles to the bound specific biochemical substance to thereby increase the sensitivity of the sensor.

48. A method according to claim 47; wherein the suspended fine particles are modified by a biochemical substance having an affinity to a specific biochemical substance to be analyzed.

49. A method according to claim 48; wherein the fine particles are composed of latex.

50. A method for analyzing biochemical substances contained in a sample liquid by utilizing a sensor comprised of a receptor for selectively reacting with a plurality of different biochemical substances specific for the receptor to bind thereon the specific biochemical substances, and a piezoelectric resonator integrated with the receptor for converting the amount of the specific biochemical substances bound to the receptor into a resonant frequency shift thereof, the method comprising the steps of: mounting the sensor in a container; contacting the sensor with a sample liquid within the container to selectively bind a plurality of different specific biochemical substances contained in the sample liquid to the receptor of the sensor; measuring a first resonant frequency of the sensor resonator within another liquid held in the container; exposing the sensor to an eluting liquid within the container to selectively elute one of the different biochemical substances bound to the sensor receptor to remove therefrom said one of the different biochemical substances; measuring a second resonant frequency of the sensor resonator within another liquid held in the container; and determining the amount of said one of the different biochemical substances selectively eluted from the sensor receptacle according to the resonant frequency shift between the first and second resonant frequencies.

51. A method according to claim 50; including the steps of successively exposing the sensor to different eluting liquids to successively elute the different biochemical substances bound to the sensor receptacle; and measuring first and second resonant frequencies before and after each of the successively exposing steps.

52. A method according to claim 50; wherein the sensor is contacted with a sample liquid containing different species of Mouse IgG.

* * * * *